United States Patent [19]

Friedman

[11] Patent Number: 5,503,164
[45] Date of Patent: Apr. 2, 1996

[54] DEVICE AND METHOD FOR REPAIR OF CRANIOMAXILLOFACIAL BONE DEFECTS INCLUDING BURR HOLES

[75] Inventor: Craig D. Friedman, East Haven, Conn.

[73] Assignee: Osteogenics, Inc., Barrington, Ill.

[21] Appl. No.: 188,485

[22] Filed: Jan. 28, 1994

[51] Int. Cl.⁶ .............................. A61B 19/00; A61F 2/28
[52] U.S. Cl. ............................ 128/898; 128/897; 623/16
[58] Field of Search ................................... 128/897, 898; 623/16–23; 600/86, 87–89, 92, 93, 95, 99

[56] References Cited

U.S. PATENT DOCUMENTS

| 4,745,914 | 5/1988 | Frey et al. | 623/16 X |
| 4,917,702 | 4/1990 | Scheicher et al. | 623/16 |
| 4,976,728 | 12/1990 | Willert et al. | 623/16 X |
| 5,139,497 | 8/1992 | Tilghman et al. | 623/16 X |
| 5,336,264 | 8/1994 | Constanz et al. | 623/16 |

Primary Examiner—Angela D. Sykes
Assistant Examiner—Samuel Gilbert
Attorney, Agent, or Firm—Baker & Botts

[57] ABSTRACT

An apparatus for the repair of craniomaxillofacial bony defects is described comprising a biocompatible scaffolding with an insert segment positioned at the proximal surface of the bone defect and stabilized with support means, coupled with bone replacement material applied distal to the scaffolding insert segment and generally filling the defect. Most preferably, the bone replacement material is a low temperature-hardening, gradually resorbable hydroxyapatite forming cement. Also taught are surgical methods for the repair of craniomaxillofacial bony defects employing the inventive scaffolding and scaffolding/bone replacement material composite; and kits including the scaffolding and the bone replacement material and/or starting materials for their preparation.

37 Claims, 6 Drawing Sheets

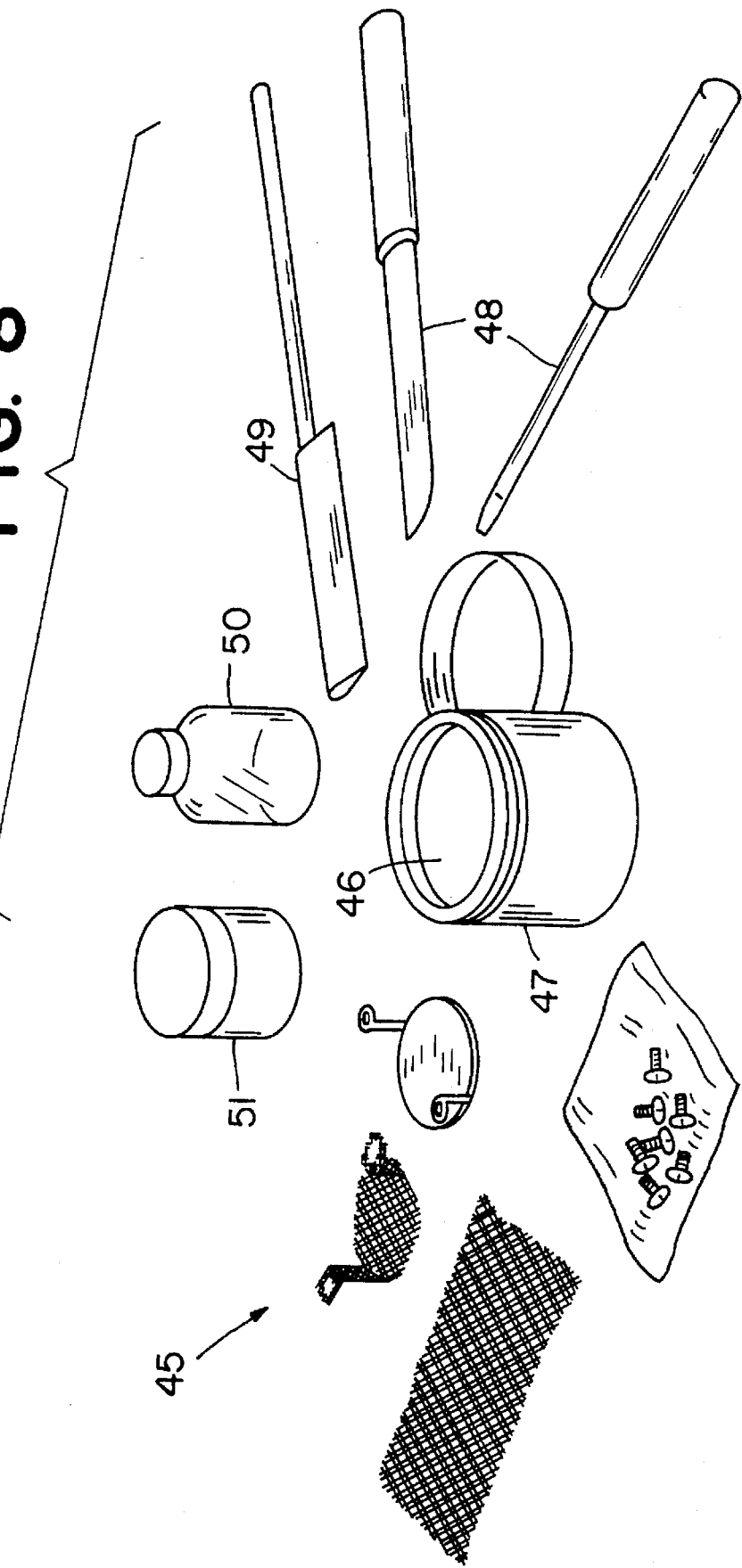

DEVICE AND METHOD FOR REPAIR OF CRANIOMAXILLOFACIAL BONE DEFECTS INCLUDING BURR HOLES

BACKGROUND OF THE INVENTION

1. Field of the Invention

This invention relates to the repair of bone defects in the cranium or in facial or maxillofacial bones. In particular, it relates to a specific restorative combination of scaffolding and bone replacement material which is used to repair such defects, to the scaffolding itself, and to the associated methods, surgical techniques, medical devices and kits.

2. Discussion of the Prior Art

A variety of devices and materials have been used in attempts to repair bone defects. Metal plates have been employed to repair cranial defects for centuries. However, contour reconstruction of the non-stress-bearing craniomaxillofacial skeleton continues to be a technical and materials science problem. Metals are difficult to shape and are hampered by disadvantages such as infection and corrosion. Polymers are often encapsulated by scar tissue, resulting in significant rates of implant infection and/or extrusion. Autogenous bone grafts and other biological materials may cause donor site morbidity, may exhibit significant post implantation resorption, and are troublesome to accurately form to skeletal defects.

Of the alloplastic materials used to augment and replace the craniomaxillofacial skeleton, the most promising and best tolerated are calcium phosphate-based compounds. Since the mid-1970's, a variety of preformed calcium phosphate materials in the form of hydroxyapatite have been used in clinical applications within medicine and dentistry. To some extent, the applicability of these preparations has been limited because they had to be preformed as hard materials. These ceramic forms of hydroxyapatite are heated to fuse individual crystals to each other through a process called sintering. This results in a tough, functionally non-resorbable material available in dense or porous forms. See Costantino and Friedman et al., "Hydroxyapatite Cement: I. Basic Chemistry and Histologic Properties," 117 Arch. Otolaryngol. Head Neck Surg. 379 (April 1991).

Most of these implants have been in the form of prefabricated, sintered hydroxyapatite in either granule or block forms. These preparations have several drawbacks, including a limited ability to conform to skeletal defects, particularly in the case of blocks; inadequate structural integrity of granules (which do not bond together), and difficulty in modeling the implant to the shape of missing skeletal tissue with both blocks and granules. The block form of hydroxyapatite provides structural support, but among other complications, must be held in place by mechanical means, which greatly limits its use and its cosmetic results; and it is very difficult to saw a shape such that it fits the patient's individual defect. The granular form produces cosmetically better results, but has a very limited structural stability and is difficult to contain during and after a surgical procedure. All of these products are ceramics, produced by high temperature sintering, and are not individually crystalline, but rather have their crystal boundaries fused together. These ceramic-type materials are in general functionally biologically non-absorbable (having an absorption rate generally not exceeding on the order of 1% per year).

A porous, non-resorbable material based on coral allows intergrowth with bone, but ultimately becomes only approximately 20% bone with the remaining 80% subsisting as scar tissue. "HA RESORB" made by Osteogen is a form of absorbable apatite, but is not a cement and is not entirely composed of hydroxyapatite. It is granular and not adhesive. "HA RESORB" is loosely rather than adhesively packed into place. It is resorbed quickly and may result in defect formation. In the dental materials market, "HAPSET" is a composition of calcium phosphate granules and cementable plaster of Paris (calcium sulfate). This material is not truly a hydroxyapatite cement and contains too much calcium sulfate for most biological uses. The calcium sulfate component of such a composition is resorbable, but not the calcium phosphate granules.

One alternative which has been proposed is a composite formed of a biocompatible metal, such as titanium, tantalum or niobium, mixed as a powder with powdered ceramic calcium phosphates and then pressed or sintered into an implant. See U.S. Pat. No. 4,599,085 (Riess et al.).

A specific but fairly common bone repair problem in the cranial area is the repair of burr holes after a craniotomy. Burr hole defects after craniotomy can easily be detected by the naked eye shortly after an operation; they may cause retraction of the skin and are cosmetically unappealing. Thus, in modern neurosurgical operations, the repair of burr holes is an important end step to the craniotomy.

Attempts at burr hole repair have included the use of different metals such as aluminum, gold, vitallium, tantalum and stainless steel. Also, compositions of plastic, acrylic resin and ceramics have been employed. Frozen lyophilized human cadaver bone, chips of autogenous bone, and coral have been used to fill burr holes. Attempted plugging of burr holes with autologous bone plugs formed with rongeur, mostly from the temporal bone, is another technique that has been employed. All of these approaches have been unsatisfactory to some degree. Local irritation, failure to achieve good cosmetic results, additional surgical time or insufficient sources of cylindrical bone plugs have been some of the difficulties encountered. Use of a specialized burr hole saw for simultaneous production of burr holes and appropriate autologous bone plugs which can readily be reinserted and locked in place using bone dust and Tiscel glue has also been described. Bostrom et al., "Reconstruction of Craniotomy Burr-Holes with Autologous Bone Blugs [sic] Made by a New Hole-Saw," 105 Acta Neurochir. 132 (1990). Examples of metal plates for burr hole repair by bridging the outer surface of the defect are the micro burr hole covering and bone flap fixation plates from Leibinger GmbH. See "Titanium Micro System," Leibinger GmbH 1992. Titanium micromesh for defect-bridging outer surface reconstruction of bony structures is illustrated in the same brochure. See also the larger scale "DUMBACH TITAN MESH-SYSTEM" ("DTM") of Osw. Leibinger GmbH (1990), which may be employed with autogenous spongiosa, granulated demineralized pyrolized bone and hydroxylapatite granulate if desired.

Recently, a new type of calcium phosphate cement that sets to hydroxyapatite in vivo has been developed. See U.S. Pat. Nos. Re. 33,221 and Re. 33,161 to Brown and Chow. This is essentially a bone replacement or bone substitute cement which can be applied intraoperatively as a paste and subsequently sets to a structurally stable implant material composed of microporous hydroxyapatite. This is a nonceramic form of hydroxyapatite cement which is produced by direct crystallization of hydroxyapatite in vivo, and does not require heating for the formation of a structurally stable implant. These new hydroxyapatite-forming cements are biologically compatible and are self-hardening to form a mass with sufficient strength for many medical and dental applications. When implanted in bone, the cement resorbs slowly and is gradually replaced by new bone formation with negligible loss in the volume or integrity of the tissue that receives the implant. See also U.S. patent application Ser. No. 08/030,709, filed Mar. 13, 1993. The material of Brown and Chow has been employed, e.g., to reconstruct two centimeter diameter calvarial defects in cats. The calcium phosphate cement was gradually replaced by bone, instead of being fully resorbed without bone deposition or remaining as a permanent implant. See Chow, Takagi, Costantino and Friedman, "Self-Setting Calcium Phosphate Cements," 179 Mat. Res. Soc. Symp. Proc. 3 (1991). A virtually identical calcium phosphate system which consists of tetracalcium phosphate and monocalcium phosphate or its monohydrate form was described by Constantz et al. (Compare U.S. Pat. Nos. 5,053,212; 5,129,905 and 5,178,845). This cement system is believed to involve, in some embodiments, conversion of the monocalcium phosphate to dicalcium phosphate which reacts with tetracalcium phosphate to form hydroxyapatite.

SUMMARY OF THE INVENTION

It has now been discovered that the repair of many craniomaxillofacial bony defects may be improved through the use of a biocompatible scaffolding with an insert segment positioned at the proximal surface of the bone defect and stabilized with support means, coupled with a bone replacement material applied distal to the scaffolding insert segment and generally filling the defect. Most preferably, the bone replacement material is a bone replacement cement applied in paste form.

One aspect of the invention is an apparatus comprising a scaffolding to support a bone replacement material for the repair of craniomaxillofacial bone defects, where the scaffolding is of a biocompatible material and comprises an insert segment that is relatively thin compared to the depth of the defect and which approximates in contour and in conformation of its perimeter the proximal surface of the missing bone. The apparatus further comprises means to support the insert segment in its desired position at the proximal bone surface of the defect. More preferably, the insert segment is comprised of a biocompatible metal, metal oxide or metal alloy and the apparatus further comprises a stabilization segment which is relatively thin compared to the depth of the defect and is disposed at least in part on the distal surface of the bone surrounding the defect. Often, the stabilization segment will be in a plane roughly parallel to the insert segment. The apparatus also comprises a connecting segment, which is preferably approximately perpendicular to the planes of both insert and stabilization segments, and which connects the insert segment to the stabilization segment so that the perpendicular distance between the two is less than, or more preferably about equal to the depth of the craniomaxillofacial bone defect. The preferred material for the scaffolding is comprised of titanium micromesh; and, most preferably, the insert segment, stabilization segment and connecting segment are all formed from a unitary piece of titanium micromesh.

The invention further contemplates a composite comprising the scaffolding apparatus having its insert segment overlayed with the bone replacement material contoured to fill the space bounded by the sidewalls of the craniomaxillofacial bone defect, the insert segment of the scaffolding and the distal surface of the defect. Examples of bone replacement materials useful in the invention include calcium phosphate based materials, silicate acrylic salts, sintered hydroxyapatite granules, replaminform (or corralinc) hydroxyapatite, apatitc granules and biocompatible osseoconductive polymers. The bone replacement material is preferably a biocompatible self-setting at least partially resorbable hydroxyapatite cement; and the scaffolding is preferably comprised of an osseointegrative metal, most preferably titanium.

The invention further includes a surgical method for the repair of craniomaxillofacial bone defects, particularly full thickness craniomaxillofacial skeletal defects comprising inserting the insert segment of a scaffolding apparatus into the defect with the insert segment approximately flush with the base of the defect, affixing the scaffolding to the surrounding bone with stabilization means, filling the remainder of the defect with bone replacement material, and contouring the material as needed to approximate the distal surface of the missing bone. In an additional embodiment, the invention comprises a kit including the scaffolding and the bone replacement material, and/or starting materials for their preparation.

The apparatus and method may be employed to repair a variety of craniomaxillofacial defects, especially full thickness craniomaxillofacial skeletal defects, particularly burr holes.

A number of objects and advantages characterize the invention. The inventive apparatus and method provide a scaffolding, i.e., floor or grid, upon which the bone replacement material to repair maxillocraniofacial bone defects is applied. While, e.g., bone replacement cement paste may be used to fill cranial burr holes directly, if there is not dura directly below the burr hole, the cement can extrude intracranially. The scaffolding insert segment prevents overfilling intracranially.

The inventive apparatus and surgical technique are also easy to use and convenient for the surgeon intraoperatively. Burr holes and other similar cranial defects can be rapidly filled with bone replacement material in just a few seconds. In the case of burr holes, the invention reliably allows 14 millimeter burr holes to be filled by 2 to 2.5 grams of self-setting hydroxyapatite cement. In addition, the bone replacement material when applied over the scaffolding achieves the appropriate contour, strengthens the reconstructed area, and seals the intracranial space from the extracranial environment.

A further advantage of the inventive apparatus is that it does not require that screws be used to hold the insert segment in place. When a bone replacement cement is used, fixation of the scaffolding may be achieved by the cement as and after it sets. However, other support means, including screw fixation of extensions or tabs connected to the insert segment, are also contemplated.

BRIEF DESCRIPTION OF THE DRAWINGS

FIG. 8 shows an embodiment of an inventive kit comprising scaffolding and bone replacement material.

DESCRIPTION OF THE PREFERRED EMBODIMENTS

The complete disclosures of U.S. Pat. Nos. Re. 33,221 and Re. 33,161 and pending U.S. patent application Ser. No. 08/030,709, filed Mar. 13, 1993, are expressly incorporated herein by reference.

Figure 1A:
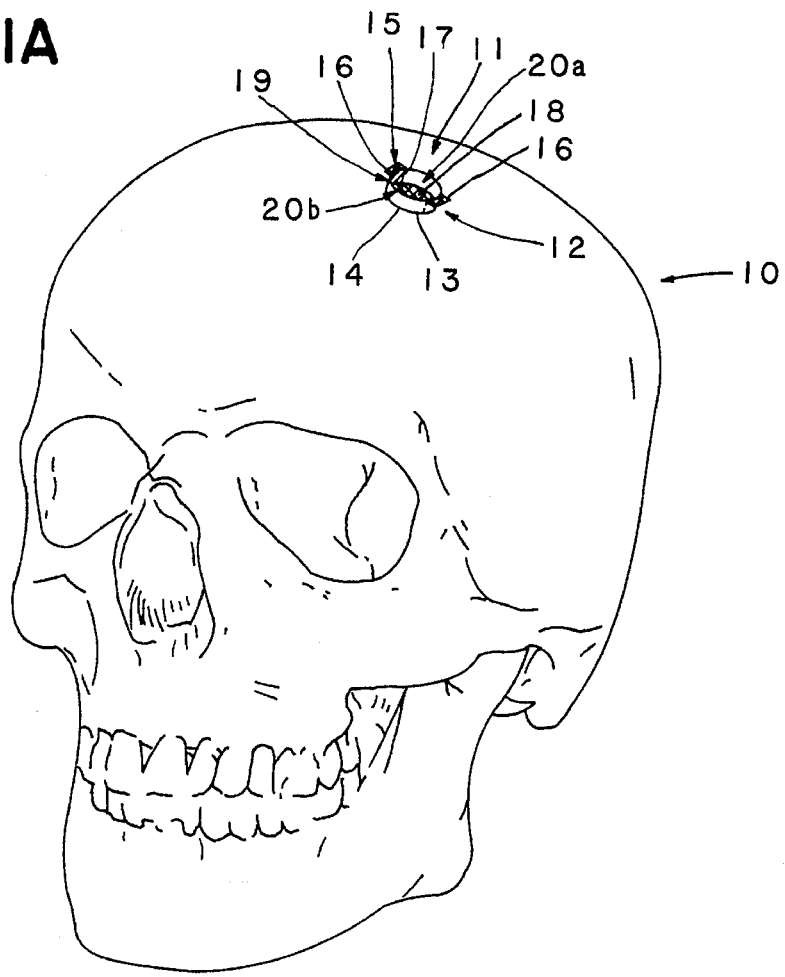
FIG. 1A illustrates in perspective a cranial defect with an embodiment of the inventive scaffolding in position.
Figure 1B:
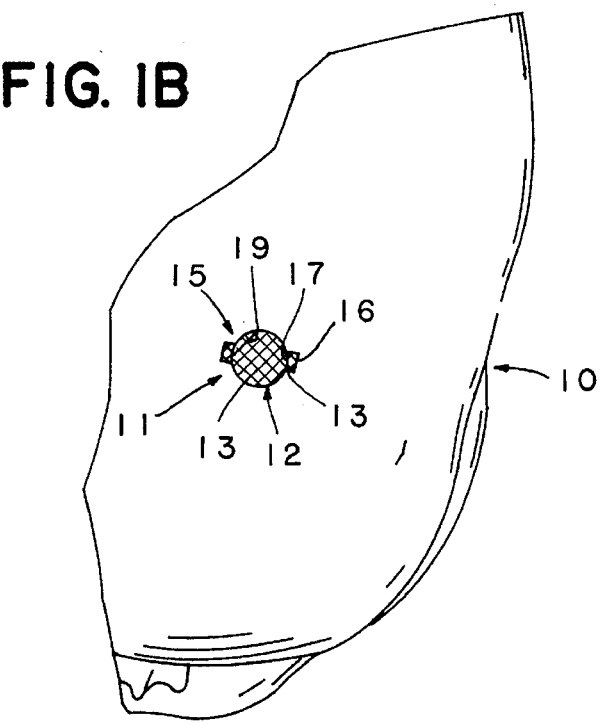
FIG. 1B is a top view of the scaffolding in position, illustrating metal micromesh material for forming the scaffolding.

Referring to FIGS. 1A and 1B, the craniomaxillofacial bone 10 sustains a defect 11. The defect depicted in the FIGURE is a burr hole, but the invention is suitable for repair of other craniomaxillofacial defects, e.g., at the orbital floor, orbital rim, mastoids, maxilla and cranioplasty. The inventive scaffolding, generally 12, is seated in the defect with a relatively thin insert segment 13 having conformation and contour of its perimeter 14 approximating the proximal surface of the missing bone. Means, generally 15, are employed for supporting the insert segment in position at the proximal bone surface of the defect 20b. In FIG. 1A and 1B, the supporting means are illustrated as a stabilization segment or tab 16, shown in the figure as rectangular, which laps over onto the distal surface of the cranium in one or more positions at the edge of the defect. The stabilization segment 16 is attached to the insert segment 13 of the scaffolding 12 by connecting segment 17. Connecting segment 17 is relatively rigid and approximately perpendicular to the plane of the insert and stabilization segments. The entire scaffolding including insert segments and support means is preferably formed of a biocompatible metallic mesh 18. The scaffolding insert segment 13 together with the sidewalls of the bony defect 19, and the distal surface of the defect where bone was previously present or should have been present 20a, define the space for insertion of the bone replacement material.

FIG. 1B provides a perpendicular top view of the scaffolding in one embodiment in which the scaffolding is formed of the preferred titanium micromesh. Most preferably, the micromesh is of 0.1 to 0.2 millimeters thickness; i.e., it is relatively thin compared to the depth of the bony defect in craniomaxillofacial applications for which this repair is suited.

Figure 1C:
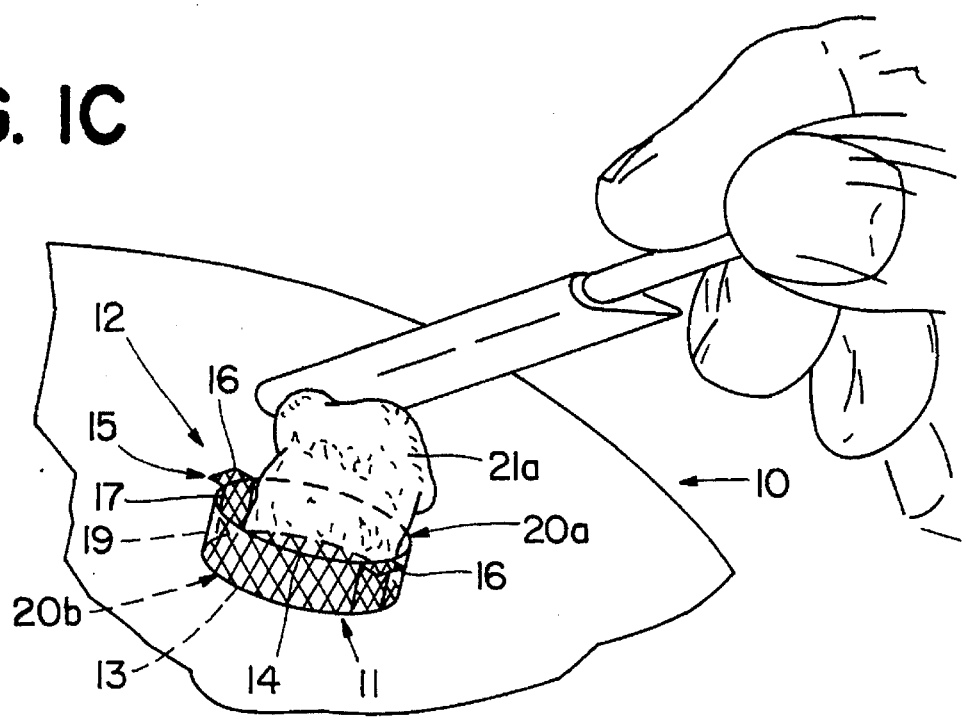
FIG. 1C depicts the deposition of bone replacement cement paste material in the space bounded by the scaffolding insert segment and the sidewalls of the bony defect.

The method of the invention, see FIG. 1C, is a surgical method for the repair of a craniomaxillofacial bone defect comprising inserting the scaffolding described above into the bony defect 11 with the insert segment 13 approximately flush with the proximal base of the defect 20b, stabilizing the scaffolding to the surrounding bone with stabilization means 15, filling the remainder of the defect with bone replacement material 21a, and contouring it appropriately.

Figure 1D:
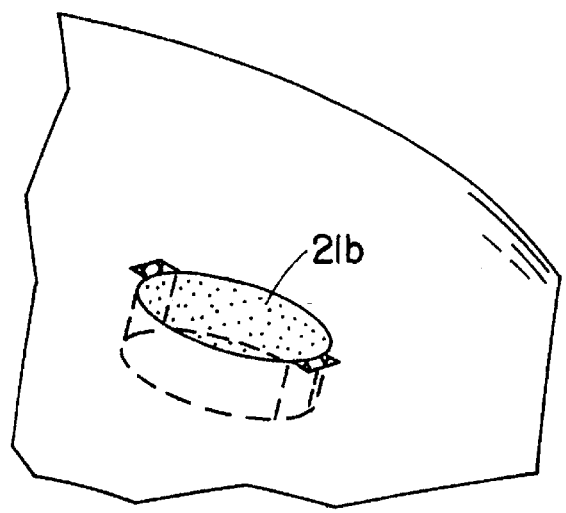
FIG. 1D illustrates the completed bony defect repair with the distal surface of the bone replacement material contoured and smoothed to replicate the contour of the distal surface of bone missing at the defect.

The composite comprising the scaffolding apparatus with bone replacement material in place 21b, contoured and hardening is illustrated in FIG. 1D.

Figure 2:
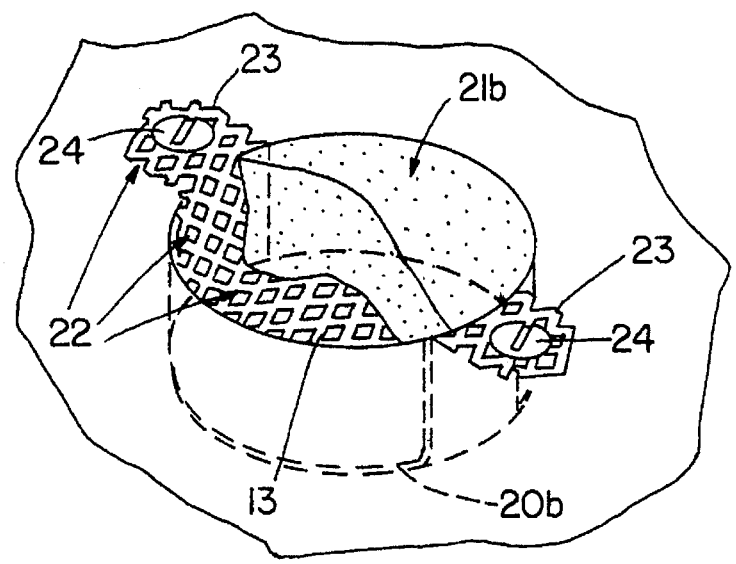
FIG. 2 is a perspective view of a burr hole repaired in accordance with the invention; the stabilization segment comprises two tapered tabs fixed into the healthy bone with metal screws. The bone replacement cement illustrated in this figure is partially cut away to permit visualization of the entire inventive apparatus.

With reference to FIG. 2, the scaffolding 22 may comprise a variety of means for stabilizing the insert segment 13 at the proximal surface of the bony defect 20b. An alternative to the rectangular overlap tabs 16 of FIG. 1 is illustrated as tapered overlap tabs 23 in FIG. 2 which lie on the distal surface of the cranium at the perimeter of the defect and are fixed in place with screws 24, preferably of metal or metal alloy. In the figure, the inventive scaffolding is seated in a burr hole and bone replacement cement 21b has been partially cut away in the figure to better illustrate the invention.

Figure 3:
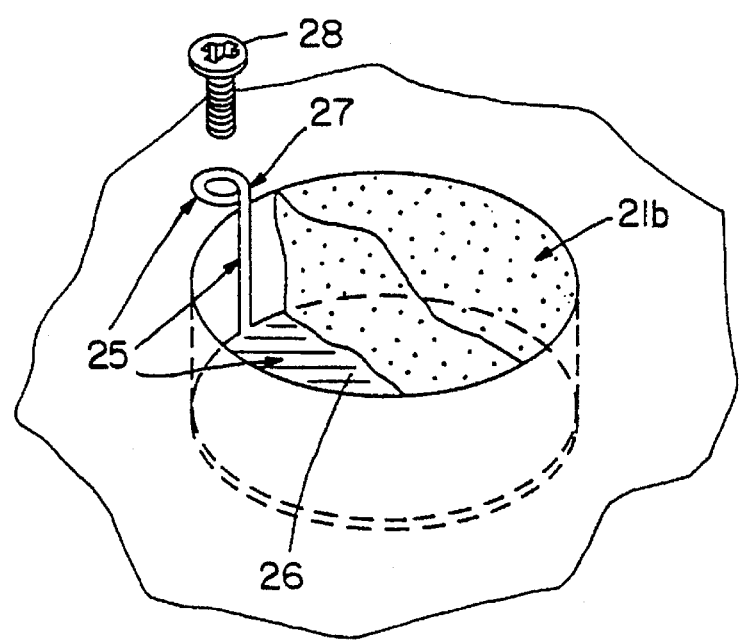
FIG. 3 is a perspective view of a scaffolding with a unitary loop for receipt of a metal stabilization screw. This scaffolding is again placed in a burr hole and the bone replacement material is partially cut away to better illustrate the combined apparatus.

FIG. 3 illustrates another alternative embodiment of the invention in which the scaffolding 25 comprises an insert segment which is a plate 26 integrally formed with a projection and screw seat 27 which together with the screw 28 affixes the scaffolding to the bone near the defect and stabilizes it in position. The bone replacement material 21b is once again cut away in the figure for illustrative purposes.

Figure 4:
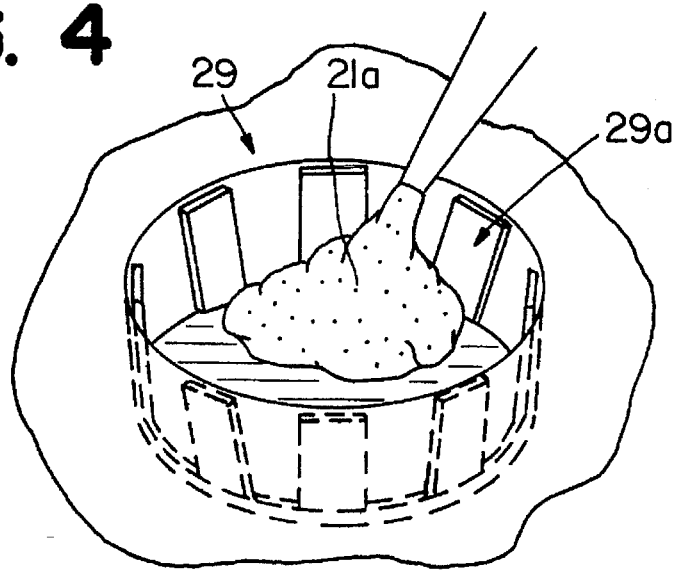
FIG. 4 shows a scaffolding with stabilization segments comprising flange means that are relatively stiff, but bendable under manual pressure, and biased against approximately opposing sidewalls of the bony defect so as to form a resilient stabilization means for the scaffolding while the cement paste is inserted.

In FIG. 4, a scaffolding 29 is seated in a craniofacial defect in accordance with the invention and is stabilized in position by the externally biased resilient perimeter of the insert segment, or a portion thereof, bent distally. In the figure, cement 21 a is in the process of being poured, injected, squirted, spatulated, spooned or otherwise introduced into the defect on top of the scaffolding and will itself serve as a principal aspect of the means for stabilizing the scaffolding in the desired position. The cement also serves this purpose in other embodiments of the invention.

Figure 5:
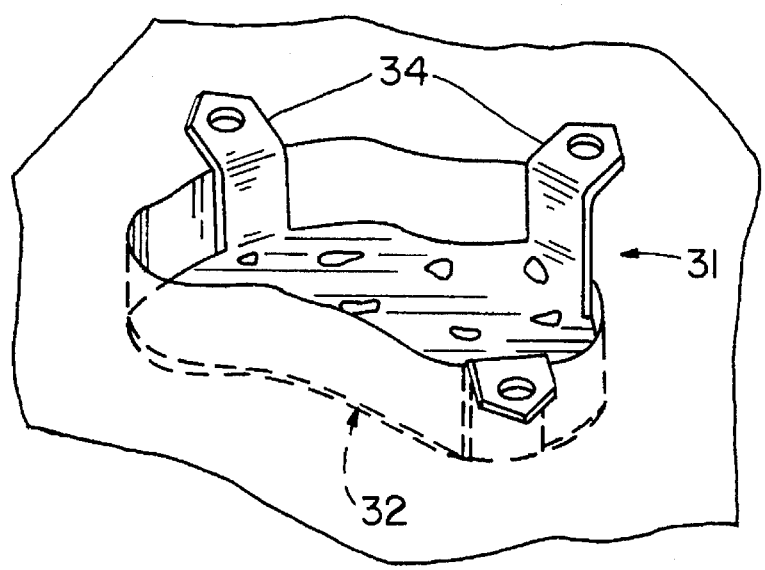
FIG. 5 illustrates the inventive repair apparatus in an embodiment in which the perimeter of the bony defect and the perimeter of the insert segment are asymmetrical, the insert segment itself is perforated in an asymmetrical pattern, and more than two stabilization means, in the form of tabs overlapping onto the distal surface of the peripheral bone, are employed.

As shown in FIG. 5, neither the craniomaxillofacial defect nor the scaffolding need be symmetrical for purposes of the invention. This figure depicts an asymmetrical bony defect with an asymmetrical scaffolding 31. The perimeter 32 of the inlet segment approximates the perimeter of the defect. In addition, the insert segment of the scaffolding may be asymmetrically perforated. The means for stabilizing the insert segment in this embodiment comprises multiple tabs 34 which are relatively rigidly connected to the insert segment with connecting segments roughly perpendicular to the insert segment's plane and which are bent at 90 degrees at a height equal to the depth of the cranial defect so as to form overlapping tabs on the surface of the bone peripheral to the defect.

Figure 6:
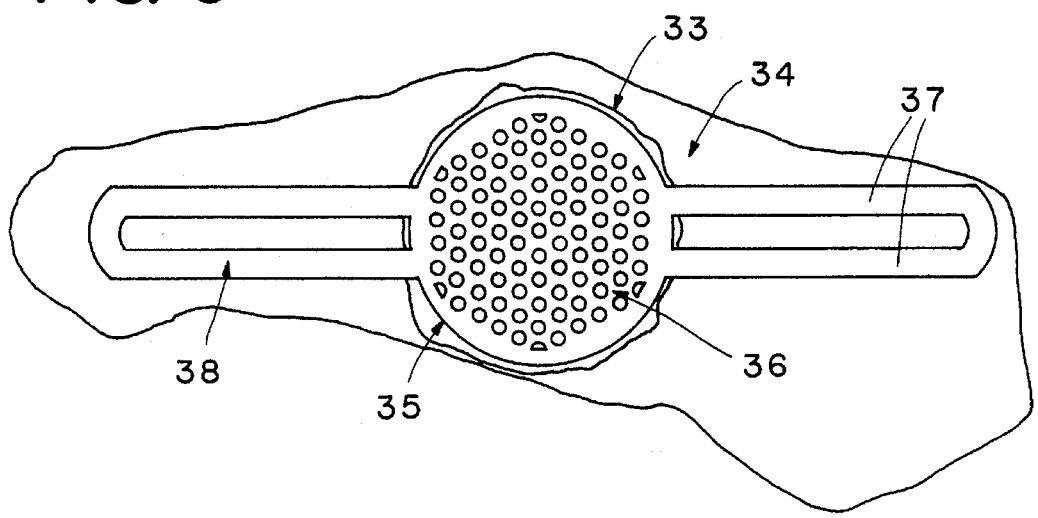
FIG. 6 illustrates the invention in a different area of the craniomaxillofacial skeleton, namely, the orbital rim.

FIG. 6 illustrates the preferred embodiment of the invention in this case applied to repair a defect in another craniomaxillofacial location namely, the orbital rim. In FIG. 6, a defect 33 in the orbital rim 34 is fitted with a preferred scaffolding 35 comprising a micromesh insert segment 36 approximating the proximal surface of the missing bone in conformation and contour. Slotted flanges or loop shaped extensions 37 attached to the insert segment comprise a supporting means 38 and are bendable anywhere along their length to form the stabilization segment and connecting segment. The dimensions of the slots in the flanges or extensions are suitable for receipt of screws employed in craniomaxillofacial bone repair. The threaded portion of the screw can pass through the opening, while the head of the screw is too large to fit through the opening and thus anchors the loop shaped extension in place.

Figure 7:
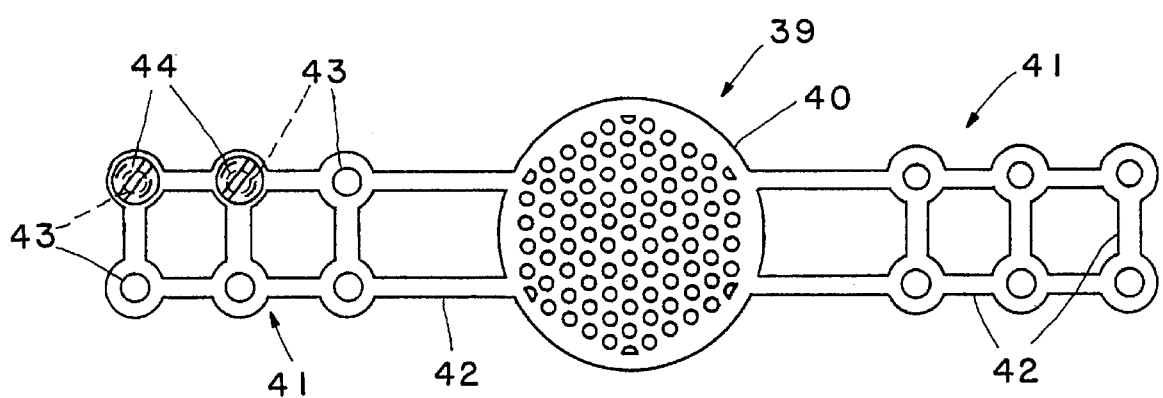
FIG. 7 depicts an alternative burr hole repair scaffolding.

FIG. 7 illustrates a burr hole repair scaffolding 39 with insert segment 40 and with supporting means 41 extending therefrom, and also including a connected grid 42 of screw receiving ports 43 containing screws 44. The preferred dimensions for the holes in the scaffolding, both in the insert segment and in the stabilization segments are from 1 to 1.2 mm.

FIG. 8 illustrates an embodiment of the contents of an inventive kit for the repair of craniomaxillofacial defects comprising a selection of one or more scaffoldings 45 and a bone replacement material for use therewith 46 in an appropriate container 47. The kit may also contain, for example, other items which may be useful or convenient for the surgeon such as tools for trimming (e.g., knife or scissors), bending or inserting the scaffolding 48, delivery means 49 (e.g. syringe, spatula, spoon, squeeze tube) for the bone replacement material, a liquid phase 50 for formulation of a bone replacement cement from a powdered bone replacement cement precursor, additives 50 which may be useful with the bone replacement material in specific situations, such as antibiotics, bone growth proteins, viscosity modifiers, demineralized bone, bone dust, etc.

A wide variety of choices is available for the insert segment of the scaffolding or platform which is recessed within the bone defect and acts as a floor upon which the bone replacement material can be applied. Any metal or other substance which is used should be biocompatible. Examples of appropriate materials include metals and metal alloys, ceramics, oxides, and preformed implants of bone replacement cement. Examples of metals which may be used include surgical stainless steel, vitallium, cobalt-molybdenum alloys, titanium and titanium alloys, e.g., titanium aluminum alloy. Ceramic scaffoldings may for example be made of calcium phosphate (e.g., hydroxyapatite, tricalcium phosphate) silicate, aluminum oxide, or combinations of materials. The preferred materials for the scaffolding are osseointegrative, and the most preferred material is titanium.

The form of the insert segment or platform may be any mechanically and biologically suitable form, including that of a plate, a perforated plate, a mesh, a relatively thin plug, a screen, or a grid. The stabilization means may be formed of the same material as the insert segment of the scaffolding, or may be of different biocompatible materials. The inventive scaffolding and its parts can be comprised of a single biocompatible material such as the preferred titanium mesh, or of two or more materials. The most preferred scaffolding material is titanium micromesh, such as the titanium micromesh described above available from Leibinger GmbH.

Bone replacement materials useful in the invention include calcium phosphate based materials such hydroxyapatite cements, silicate acrylic salts such as Ionos cement, sintered hydroxyapatite granules, replaminform (or corraline) hydroxyapatite, apatite granules such as those of Osteogen and biocompatible osseoconductive polymers (available in Europe from DTI Corporation).

The bone replacement or bone substitute cement which is preferably employed as an aspect of this invention is of the variety of calcium phosphate-based cements which self-harden substantially to microcrystalline, non-sintered hydroxyapatite at a temperature tolerable to body tissues, is osseoconductive and gradually resorbable, and is gradually replaced at least in significant part on a roughly one to one basis by bone when placed in contact with living bone. The term "low temperature-hardening gradually resorbable hydroxyapatite forming cement" will be employed hereinafter to refer to this material.

A preferred cement is that of Brown and Chow described in U.S. Pat. Nos. Re. 33,161 and 33,221. The preferred major components of the calcium phosphate cement of Brown and Chow are tetracalcium phosphate (TTCP) and dicalcium phosphate anhydrous (DCPA) or dicalcium phosphate dihydrate (DCPD). These react in an aqueous environment to form hydroxyapatite (HA), the principal mineral component of teeth and bones, as the final product.

The chemical reaction that occurs during the setting of the TTCP-DCPA (or TTCP-DCPD) cement described in Brown and Chow can be represented by the following equation:

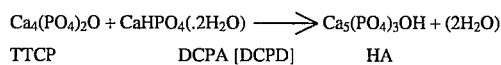

$$Ca_4(PO_4)_2O + CaHPO_4(.2H_2O) \longrightarrow Ca_5(PO_4)_3OH + (2H_2O)$$
TTCP    DCPA [DCPD]    HA Rapid HA formation and concomitant dissolution of both cement ingredients, TTCP and DCPA, lead to the hardening of the cement ordinarily within 30 minutes or less.

Most preferred are the improved bone replacement cements described as follows in pending U.S. patent application Ser. No. 08/030,709, filed Mar. 12, 1993, which contemplates use of tetracalcium phosphate precursor that has been maintained in a relatively anhydrous environment prior to its use, and/or prepared with a calcium to phosphorus ratio of less than 2%:

According to Ser. No. 08/030,709, if the prepared tetracalcium phosphate has a molar Ca/P ratio above 2, calcium oxide is believed to be present in the material as an impurity phase. When such a tetracalcium phosphate sample is used in the cement, the rapid dissolution of the CaO causes the pH of the cement slurry to rise substantially above pH 8.5 (but below 12), which impedes the setting reaction.

It was also found that tetracalcium phosphate is extremely reactive to water. Thus, when exposed to air, tetracalcium phosphate has been found to react with the moisture present in the air to form a small amount of hydroxyapatite (OHAp) and calcium hydroxide or calcium oxide. It was discovered that these products coat the surfaces of the tetracalcium phosphate crystals and cause the tetracalcium phosphate particles to become significantly less reactive when used in the cement system. By maintaining tetracalcium phosphate in an anhydrous environment, the undesirable surface contamination by the aforementioned reaction products is minimized. Self-setting calcium phosphate cements with substantially improved setting times and mechanical strengths were obtained when tetracalcium phosphate prepared under anhydrous conditions was used.

The undesirable reaction of tetracalcium phosphate with moisture is irreversible at later stages in its preparation so that drying the moisture-exposed tetracalcium phosphate to remove the water was not found to suffice to reclaim the properties of uncontaminated tetracalcium phosphate.

Tetracalcium phosphate has the formula $Ca_4(PO_4)_2O$, and a theoretical ideal molar Ca/P ratio of 2.0. Its traditional mode of preparation is illustrated in the following equation:

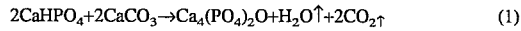

$$2CaHPO_4 + 2CaCO_3 \rightarrow Ca_4(PO_4)_2O + H_2O\uparrow + 2CO_2\uparrow \qquad (1)$$

It is thermodynamically stable only at temperatures above approximately 1400° C.

In Ser. No. 08/030,709, the preferred preparation of tetracalcium phosphate powder for cement use is illustrated by the following steps:

EXAMPLE 1

Preparation of tetracalcium phosphate in a furnace: One first prepares a homogenous mixture that has a Ca/P ratio of less than 2, heats the mixture to 1400° C. or above, and then maintains the sample at that temperature for a sufficiently long period of time, for example 6 hours, to assure as complete conversion as possible of the starting mixture to tetracalcium phosphate. An example of the starting mixture would consist of 2 moles of $CaHPO_4$ (272 grams) and 1.8 moles of $CaCO_3$ (180 grams). The excess $H_2O$ and $CO_2$ are expelled in the heating process.

One may also use any other types of calcium and phosphate containing compounds to prepare mixtures with a molar Ca/P ratio of less than 2 provided that the non-calcium and non-phosphate components in the mixture can be expelled by evaporation during the firing with or without an accompanying oxidation reaction. For example, the following reactions may be employed with appropriate adjustment of the molar ratios:

$$2CaHPO_4 + 2CaO \rightarrow Ca_4(PO_4)_2O + H_2O\uparrow \qquad (2)$$

$$Ca_2P_2O_7 + 2CaO \rightarrow Ca_4(PO_4)_2O \qquad (3)$$

$$Ca_3(PO_4)_2 + Ca(OH)_2 \rightarrow Ca_4(PO_4)_2O + H_2O\uparrow \qquad (4)$$

$$4CaO + 2(NH_4)_3PO_4 \rightarrow Ca_4(PO_4)_2O + 6NH_3\uparrow + 3H_2O\uparrow \qquad (5)$$

$$2CaHPO_4 + 2Ca(CH_3CO_2)_2 + 4O_2 \rightarrow Ca_4(PO_4)_2O + 7H_2O\uparrow + 4CO_2\uparrow \qquad (6)$$

The preparation of the mixture for firing is the only step in the tetracalcium phosphate synthesis in which the presence of water is not a concern. This is because the tetracalcium phosphate is formed only after the firing process.

EXAMPLE 2 (Comparative)

If the Ca/P molar ratio of the homogenous mixture prepared for firing is above 2, calcium oxide will be present as an impurity phase in the product. Thus, in the reaction represented by equation (1), if 2 moles (272 grams) of $CaHPO_4$ is combined with 2.2 moles (220 grams) of $CaCO_3$, the molar Ca/P ratio will be 2.1, and the reaction in the furnace will be:

$$2CaHPO_4 + 2.2CaCO_3 \rightarrow Ca_4(PO_4)_2O + 0.2CaO + H_2O\uparrow + 2.2CO_2\uparrow \qquad (7)$$

The presence of CaO as an impurity in the prepared tetracalcium phosphate is undesirable because during the cement setting, rapid dissolution of CaO raises the slurry pH to approximately 10 to 12, and this greatly impedes the setting reaction to the point that the cement often fails to harden.

EXAMPLE 3

While it is essential that Ca/P ratios of greater 2 should be avoided in the preferred embodiment, a mixture with a ratio of lower than 2 is permissible, as far as the cement setting reaction is concerned. This is because in such a case, the reaction impurity by-product will be hydroxyapatite. It is important to note that when hydroxyapatite is formed during the firing process, it is homogeneously dispersed in the prepared tetracalcium phosphate as a phase impurity, and the reactivity of tetracalcium phosphate is not significantly affected. This is in great contrast to the hydroxyapatite coatings that form on the tetracalcium phosphate crystals as a result of reaction with moisture. In this latter case, the hydroxyapatite is highly detrimental to the reactivity of tetracalcium phosphate. Equation (8) given below illustrates the hydroxyapatite as a by-product when a mixture with a Ca/P ratio of 1.9 is fired:

$$2CaHPO_4 + 1.8CaCO_3 \rightarrow 0.7Ca_4(PO_4)_2O + 0.2Ca_5(PO_4)_3OH + H_2O\uparrow + 1.8CO_2\uparrow \qquad (8)$$

EXAMPLE 4

A Ca/P ratio of 2 precisely is to be avoided because the inherent error in measurement of the reactants makes actual preparation of a sample with Ca/P ratio greater than 2 a statistical probability in a number of instances, and because cements prepared from tetracalcium phosphate with Ca/P ratio less than 2 were found to have greater mechanical strength than those with a ratio of 2, as illustrated in the following table:

TABLE I

Effect of the Ca/P Ratio of TTCP on Diametral Tensile Strength (DTS) of Calcium Phosphate Cement

| Ca/P Ratio of TTCP | 2.0 | 1.96 | 1.90 |
|---|---|---|---|
| DTS (MPa) Mean ± s.d. (n = 3) | 8.34 ± 0.17 | 8.06 ± 1.64 | 10.38 ± 0.44 |

To prepare the calcium phosphate cement, tetracalcium phosphate and dicalcium phosphate anhydrous were combined at a molar ratio of 1:1, and mixed with 25 mmol/L phosphoric acid at a powder to liquid weight ratio of 4.0 at ambient temperature.

Diametral tensile strength was measured as follows:

DTS measurement: 0.3 gram of calcium phosphate cement powder was mixed with 0.075 mL of liquid (powder/liquid=4), spatulated on a glass slab for 30 sec., and placed in a stainless steel mold (6 mm d×3 mm h). The top and bottom surfaces of the mold were tightly covered with glass plates and the mold was placed in a 100% humidity box kept at 37° for 4 hours. The sample was removed from the mold and placed in a small amount of water for 20 hours at 37°. The diametral tensile strength (DTS) was measured with the use of a Universal Testing Machine (United Calibration Corp., Garden Grove, Calif.) at a cross-head speed of 1 mm/min.

As a practical matter, the Ca/P ratio must remain above 1.67, or stoichiometry dictates the preparation of hydroxyapatite rather than tetracalcium phosphate. Therefore, in this context, "less than 2" should be interpreted herein to mean less than 2 but greater than 1.67.

EXAMPLE 5

Quenching of fired mixture in an anhydrous atmosphere: After heating the mixture for a sufficient length of time, the mixture must be cooled down rapidly to prevent reversion of the tetracalcium phosphate to the phases that are more stable than tetracalcium phosphate at temperatures lower than 1400° C. If the tetracalcium phosphate were cooled down slowly, for example, by letting it cool down spontaneously in a furnace that has been turned off, the product obtained would contain little tetracalcium phosphate. Instead, it would be a mixture that would additionally contain hydroxyapatite, calcium oxide, α-tricalcium phosphate, β-tricalcium phosphate, or calcium pyrophosphate, depending on the Ca/P ratio and the rate of cooling. Such a sample, if used for preparing the cement, would yield a product with poor setting and strength properties. Therefore, quenching is necessary, and it must be done under a substantially anhydrous environment. One example of a suitable anhydrous quench technique would be to place the mixture, as soon as it is no longer red hot, in a vacuum desiccator to isolate the tetracalcium phosphate from moisture. Other techniques of anhydrous quenching available to those of skill in the art may be used.

If the tetracalcium phosphate is quenched in an atmosphere that contains moisture, a reaction illustrated by equation (9) or (10) will occur and the tetracalcium phosphate crystals will become coated with the reaction products, hydroxyapatite and $Ca(OH)_2$ or CaO. Such a tetracalcium phosphate sample will have poor reactivity when used in the cement formulation.

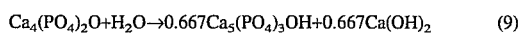

$$Ca_4(PO_4)_2O + H_2O \rightarrow 0.667Ca_5(PO_4)_3OH + 0.667Ca(OH)_2 \quad (9)$$

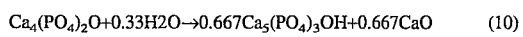

$$Ca_4(PO_4)_2O + 0.33H_2O \rightarrow 0.667Ca_5(PO_4)_3OH + 0.667CaO \quad (10)$$

Exposure to moisture at this stage will cause damage to the tetracalcium phosphate's reactivity to a significant extent, although not as critical as in the later stages of the preparation. This is because at this point, the tetracalcium phosphate is the form of chunks or lumps, with relatively small surface areas amenable to contamination, as compared with the tetracalcium phosphate that has been processed to a fine-particle state. However, moisture absorbed in the uncomminuted tetracalcium phosphate may produce an adverse effect in the comminution process as described below.

EXAMPLE 6

Particle size reduction. To produce calcium phosphate cement with the desirable properties, sparingly soluble calcium phosphates of a variety and/or mixture of particle sizes may be used. For many applications, it is preferred that the tetracalcium phosphate have at least a substantial percentage of particles, e.g., at least about 10%, of median particle size of 15 μm or below. In some applications, such as formulating an injectable root canal filler, tetracalcium phosphate with a median particle size of 1 μm or below would be preferred. Therefore, the particle size of the tetracalcium phosphate prepared in Example 5 above needs to be reduced by mechanical means. A substantially anhydrous environment during the particle size reduction process is critical. Small samples of the tetracalcium phosphate may, for example, be comminuted by hand grinding in room air for a brief period, e.g., 5 min., but long exposure to room air would be unacceptable. If the tetracalcium phosphate is ground in a ball mill, it must be done in a closed container to isolate the tetracalcium phosphate from the large volume of moist room air, or in a non-aqueous liquid that has been made anhydrous. Some of the liquids that can be advantageously employed are cyclohexane, dioxane, and absolute ethanol. Other non-aqueous liquids may also be used. Traces of water in these liquids should be removed by molecular sieve or other suitable desccicants. Liquids that should not be used include water, 95% ethanol, other alcohol solutions that contain water, acetone (which generally contains some water), etc. If one of the latter liquids is used, the ground tetracalcium phosphate will contain poorly crystallized hydroxyapatite and calcium hydroxide or calcium oxide. Such a sample will produce a poor quality cement or a cement mixture that will not harden. Once the ground tetracalcium phosphate is exposed to moisture and the reaction products coat the tetracalcium phosphate crystal surfaces, the reactivity of the tetracalcium phosphate sample cannot be rejuvenated at this point by heating and removing the adsorbed moisture.

As mentioned earlier, if the uncomminuted tetracalcium phosphate contains absorbed moisture, because of the limited surface area, the damage to the tetracalcium phosphate's reactivity as a result of hydroxyapatite coating formation would be significant but perhaps not critical. However, when such a tetracalcium phosphate sample is comminuted in an anhydrous liquid, the moisture released from the contaminated tetracalcium phosphate into the liquid will facilitate the undesirable reaction depicted by equation (9) or (10). This usually will render the tetracalcium phosphate unusable for cement formulation. If it is suspected that the uncomminuted tetracalcium phosphate has been exposed to moisture, and it is to be ground in an anhydrous liquid, it should be heated at 200° C. for 24 hours to remove absorbed moisture and cooled to room temperature in an anhydrous environment before grinding.

EXAMPLE 7

Storage of ground tetracalcium phosphate. It is important that the ground tetracalcium phosphate be stored in an anhydrous environment. Because the ground tetracalcium phosphate would have relatively large surface area, surface contamination by the reaction products with moisture will substantially compromise the reactivity of the tetracalcium phosphate and the quality of the cement. Once the surface contamination products are formed in substantial quantities, the reactivity of the tetracalcium phosphate cannot be rejuvenated by heating.

The detrimental effects of moist TTCP on the diametral tensile strength of the set cement are illustrated by Table II.

TABLE II

Diametral Tensile Strength of Calcium Phosphate Cement Prepared with Tetracalcium Phosphate that Had Been Exposed to 100% Humidity for Different Lengths of Time

| Length of Exposure in Days | Diametral Tensile Strength mean ± s.d. (n = 3) in MPa |
|---|---|
| 0 | 10.38 ± 0.44 |
| 0.2 | 8.71 ± 0.10 |
| 1 | 7.85 ± 0.13 |
| 2 | 6.66 ± 0.25 |
| 5 | 6.26 ± 0.07 |
| 16 | 2.63 ± 0.24 |

Calcium phosphate cement powders were prepared by thorough mixing of 3.66 grams of tetracalcium phosphate and 1.36 grams of dicalcium phosphate. The tetracalcium phosphate had a median particle size of 10.2 μm and had been exposed to humid air for various periods as indicated. The dicalcium phosphate had a median particle size of 0.8 μm. The diametral tensile strengths were measured following the same procedure as described earlier.

Additional properties of improved calcium phosphate cement as compared with the original calcium phosphate cement of Brown and Chow are listed in Table III:

TABLE III[1]

| | Improved CPC (TTCP Ca/P = 1.90; anhydrous prep) | Original CPC (TTCP Ca/P = 2.0) |
|---|---|---|
| Compressive strength | 64.8 ± .8 MPa (n = 3) | 36.0 ± 7 (n = 5) (Fukase, 1990)[2] |
| Diametral strength | 13.1 ± 1.3 MPa (n = 8) | 6.9 ± .3 (n = 5) |
| Setting time: Gilmore needle method | 14 min. | 25 (Brown and Chow, 1986)[3] |

[1]Moles TTCP: Moles DCPA = 1:1, powder/liquid (by wt.) = 4.0, liquid phase = 25 mmol/L $H_3PO_4$, testing conditions as per Example 4.
[2]Fukase et al., "Setting Reactions and Compressive Strengths of Calcium Phosphate Cements," J. Dent. Res. 69(12):1852–56 (1990).
[3]Brown, W. E. and Chow, L. C. (1988): A New Calcium Phosphate, Water Setting Cement, Cements Research Progress 1986, P. W. Brown, Ed., Westerville, Ohio: American Ceramic Society, pp. 352–379.

As will be recognized by those of skill in the art, other specific techniques for preparation of the tetracalcium phosphate component of this cement may be employed so long as the calcium to phosphate ratio of the tetracalcium phosphate is less than two, and/or the preparation (particularly once the tetracalcium phosphate has been comminuted) is substantially anhydrous. While either the recommended reduction in calcium to phosphate ratio or anhydrous preparation will improve the setting time and quality of the hydroxyapatite cement, the best results are obtained when both methods are practiced together. The methods can be safely practiced in a laboratory or manufacturing facility without imposing excessive additional expenses. The new methods of preparation of tetracalcium phosphate produce cements with shorter and more consistent setting times and substantially greater mechanical strengths.

The calcium phosphate cement is preferably prepared from the tetracalcium phosphate described above and one or more additional sparingly soluble calcium phosphates, particularly dicalcium phosphate anhydrous, dicalcium phosphate dihydrate, α-tricalcium phosphate, β-tricalcium phosphate, amorphous calcium phosphate, and octacalcium phosphate. Most preferably, tetracalcium phosphate is employed with dicalcium phosphate anhydrous or dicalcium phosphate dihydrate. The invention is practiced when the tetracalcium phosphate employed with the second sparingly soluble calcium phosphate compound is prepared in accordance with these conditions whether or not it is generated in situ from other precursors or passes through chemical intermediates. These compounds are contemplated as part of the composition regardless of the nomenclature used to identify them, e.g., "calcium deficient calcium phosphate compounds" instead of dicalcium phosphate.

The specially prepared tetracalcium phosphate and other sparingly soluble calcium phosphate compound(s) are combined with a liquid phase to form the useful cement, paste or slurry. The liquid phase is aqueous at least in part and may typically be water, saline, blood, dilute phosphoric acid, or one of the above with the addition of up to 10% of a calcium or phosphate source in the calcium phosphate cement powder or in the liquid phase itself. In situ liquid, e.g., at a wound site, can suffice.

EXAMPLE 8

Additional calcium phosphate cement compositions that consisted of TTCP prepared as described above and one other calcium phosphate from the group consisting of α-tricalcium phosphate (α-TCP), β-tricalcium phosphate (β-TCP), amorphous calcium phosphate (ACP), and octacalcium phosphate (OCP) were prepared with a liquid phase of 1.5 mol/L $Na_2HPO_4$. This phosphate level in the liquid phase can be attained by adding up to 10% of a phosphate salt in the calcium phosphate cement powder as described in U.S. Pat. Nos. Re. 33,161 and 33,221. Properties of calcium phosphate cements that consisted of TTCP and a calcium phosphate other than DCPA or DCPD are given in Table IV below.

TABLE IV

| Solid component | P/L[1] | DTS[2], MPa (mean ± s.d.; n = 3) | setting time (min) |
|---|---|---|---|
| TTCP[3] + 2α-TCP | 3 | 1.29 ± .26 | 25 |
| TTCP[3] + 2β-TCP | 3 | 0.22 ± .17 | 90 |
| TTCP[3] + 2 ACP | 2.5 | 0.88 ± .11 | 15 |
| 3 TTCP[3] + 2 OCP | 3 | 0.48 ± .06 | 90 |

[1]Powder to liquid ratio (by weight)
[2]Diametral tensile strength
[3]Ca/P = 1.90

The above calcium phosphate cement formulations, while not preferred because of their relatively low strengths, did harden. Some improvements in strengths are likely with adjustment of particle size, powder to liquid ratio and other parameters. These formulations did not set quickly, e.g., 2 hours, when water, saline, or a dilute phosphoric acid was used as the liquid phase in place of the 1.5 mol/L $Na_2HPO_4$.

Generally, the preferred cement will be comprised of an equimolar mixture of tetracalcium phosphate and dicalcium phosphate, although TTCP/dicalcium phosphate ratios may range from 1:1 to about 1:4. Calcium phosphate cement that has a TTCP/DCPA ratio of 1.0 will have the stoichiometry of hydroxyapatite. Experimental data now show that cement setting can occur when the ratio is as low as 0.33 or lower. Furthermore, the presence of excess DCPA does not lead to residual DCPA in the end product; the product is apatitic, probably a calcium deficient apatite that has poor crystallinity and greater solubility. Such material may have different in vivo characteristics from that of stoichiometric hydroxyapatite produced by calcium phosphate cement with a TTCP/DCPA ratio of 1.0, perhaps resorbing more rapidly in bone.

The bone replacement material, whether the preferred cement of Ser. No. 08/030,709 described immediately above or otherwise, may contain a variety of additives and beneficial agents, provided they do not interfere with its setting and bone replacement properties to any substantial degree. Examples of such additives and agents include handling agents (e.g., viscosity modifiers), extenders, crystal habit modifiers, biologically active substances, fillers and porosity agents.

The bone replacement material may be supplied to the user in a variety of forms, including as powders or as a powder mixture which is later mixed with the liquid diluent to make putty; or as a pre-mixed putty which may contain a nonaqueous extender, e.g., glycerin and/or propylene glycol. It may be supplied with or in the instrumentation which is used to introduce the cement into the body, for example, a syringe, percutaneous device, "gun", cannula, biocompatible packet, dentula, reamer, file, or other forms which will be apparent to those of ordinary skill in the art. The bone replacement material is generally provided or employed in a sterilized condition. Sterilization may be accomplished, e.g., for the preferred cement by gamma-ray radiation, typically at a dose of 2.5 Mrad.

The inventive apparatus and methods have been compared with various alternative approaches to the repair of bone defects, especially burr holes. In one type of attempted repair, a resorbable foam ("GELFOAM") was used as a floor for the cement within cranial holes 14 millimeters in diameter and 1.5 to 2.0 centimeters deep. The method was suboptimal, as the "GELFOAM" was not entirely stable and became weak very quickly when wet. Repairs were also attempted (1) with a lattice of bone grafts and plates covered with cements, or (2) with bone replacement cement located proximally and the scaffolding located distally in the repair. None of these techniques compared favorably with the inventive technique and apparatus.

It should be understood that the foregoing disclosure emphasizes certain specific embodiments of the invention and that all modifications or alternatives equivalent thereto are within the spirit or scope of the invention as set forth in the appended claims.

What is claimed is:

1. An apparatus comprising a scaffolding to support a bone replacement material for the repair of a craniomaxillofacial bone defect in which a portion of the bone is missing wherein the scaffolding is biocompatible and comprises an insert segment which is thinner than a depth of the bone defect, the insert segment having a contour and a perimeter which respectively approximate a contour and a perimeter of a proximal surface of the missing portion of the bone; and wherein the scaffolding further comprises means adapted to be disposed on a distal surface of the bone at an edge of the defect, for supporting the insert segment at a proximal surface of the bone defect.

2. The apparatus of claim 1 wherein the scaffolding is comprised of a material selected from the group consisting of a metal and a metal alloy.

3. The apparatus of claim 1 wherein the scaffolding is comprised of a material selected from the group consisting of an osseointegrative metal and a metal alloy containing an osseointegrative metal.

4. The apparatus of claim 1 wherein the scaffolding is comprised of a substance selected from the group consisting of titanium, titanium-aluminum alloy, vitallium, stainless steel, cobalt-molybdenum alloy, calcium phosphate silicate and aluminum oxide.

5. The apparatus of claim 4 wherein the scaffolding is comprised of titanium.

6. The apparatus of claim 1 wherein the scaffolding is formed from a unitary piece of titanium micromesh.

7. A composite comprising the apparatus of claim 1, wherein the craniomaxillofacial bone defect has sidewalls, the apparatus being overlaid with a bone replacement material contoured to fill a space bounded by the side walls of the craniomaxillofacial bone defect, the insert segment of the scaffolding and the distal surface of the bone defect.

8. The composite of claim 7 wherein the bone replacement material is selected from the group consisting of calcium phosphate based materials, silicate acrylic salts, sintered hydroxyapatite granules, replaminform hydroxyapatite, corraline hydroxyapatite, apatite granules and biocompatible osseoconductive polymers.

9. The composite of claim 8 wherein the bone replacement material is a calcium phosphate based material.

10. The composite of claim 9 wherein the calcium phosphate based material is a low temperature-hardening gradually resorbable hydroxyapatite forming cement.

11. A surgical method for the repair of a craniomaxillofacial bone defect in which a portion of the bone is missing comprising inserting the apparatus of claim 1 into the defect so that the insert segment is flush with the proximal surface of the bone defect; providing means for stabilizing the scaffolding to the surrounding bone; stabilizing the scaffolding with the stabilizing means; filling the bone defect with bone replacement material and contouring the material.

12. The surgical method of claim 11 further comprising adapting the apparatus of claim 1 to fit the bone defect by trimming the scaffolding.

13. The surgical method of claim 12 further comprising bending the means for supporting the insert segment to adapt it to the conformation of the defect and surrounding bone.

14. The surgical method of claim 11 further comprising inserting an orthopedic screw in the means for supporting the insert segment and into the surrounding bone.

15. The surgical method of claim 11 wherein the craniomaxillofacial bone defect to be repaired is a full-thickness craniomaxillofacial skeletal defect.

16. The surgical method of claim 11 wherein the bone defect to be repaired is selected from the group consisting of burr holes, orbital floor defects, orbital rim defects, mastoid defects, maxillary defects, and cranioplasty.

17. The surgical method of claim 16 wherein the defect to be repaired is a burr hole.

18. The surgical method of claim 11 wherein the scaffolding is comprised of a material selected from the group consisting of a metal and a metal alloy.

19. The surgical method of claim 11 wherein the scaffolding is comprised of a substance selected from the group consisting of titanium, titanium-aluminum alloy, vitallium, stainless steel, cobalt-molybdenum alloy, calcium phosphate silicate, and aluminum oxide.

20. The surgical method of claim 11 wherein the scaffolding is comprised of titanium micromesh.

21. The surgical method of claim 11 wherein the bone replacement material is selected from the group consisting of calcium phosphate base materials, silicate acrylic salts, sintered hydroxyapatite granules, replaminform hydroxyapatite, corraline hydroxyapatite, apatite granules, and a biocompatible osseoconductive polymers.

22. The surgical method of claim 21 wherein the bone replacement material is a low temperature-hardening gradually resorbable hydroxyapatite forming cement.

23. An apparatus comprising a scaffolding to support a bone replacement material for the repair of craniomaxillofacial bone defects wherein the scaffolding is biocompatible and comprises an insert segment, a stabilization segment and a connecting segment, wherein the insert segment is comprised of a material selected from the group consisting of a biocompatible metal and a biocompatible metal alloy, and is thinner than a depth of the defect, the insert segment having a contour and a perimeter which respectively approximate a contour and a perimeter of a proximal surface of a missing portion of the bone; the stabilization segment is thinner than the depth of the defect and is adapted to be disposed on a distal surface of the bone at an edge of the defect; and the connecting segment rigidly connects the insert segment to the stabilization segment.

24. The apparatus of claim 23 further comprising an opening in the stabilization segment adapted to receive a threaded portion of an orthopedic screw having a screw head, but to prevent passage of the screw head, and an orthopedic screw sized to cooperate with the stabilization segment.

25. The apparatus of claim 23 wherein the scaffolding is comprised of a material selected from the group consisting of a metal and a metal alloy.

26. The apparatus of claim 23 wherein the scaffolding is comprised of a material selected from the group consisting of an osseointegrative metal and a metal alloy containing an osseointegrative metal.

27. The apparatus of claim 23 wherein the scaffolding is comprised of a substance selected from the group consisting of titanium, titanium-aluminum alloy, vitallium, stainless steel, cobalt-molybdenum alloy, calcium phosphate silicate and aluminum oxide.

28. The apparatus of claim 27 wherein the scaffolding is comprised of titanium.

29. The apparatus of claim 23 wherein the scaffolding is formed from a unitary piece of titanium micromesh.

30. A composite comprising the apparatus of claim 23, wherein the craniomaxillofacial bone defect has sidewalls, the apparatus being overlaid with a bone replacement material contoured to fill a space bounded by the side walls of the craniomaxillofacial bone defect, the insert segment of the scaffolding and the distal surface of the bone defect.

31. The composite of claim 30 wherein the bone replacement material is selected from the group consisting of calcium phosphate based materials, silicate acrylic salts, sintered hydroxyapatite granules, replaminform hydroxyapatite, corralinc hydroxyapatite, apatite granules and biocompatible osseoconductive polymers.

32. The composite of claim 30 wherein the bone replacement material is a calcium phosphate based material.

33. The composite of claim 32 wherein the calcium phosphate material is a low temperature-hardening gradually resorbable hydroxyapatite forming cement.

34. A kit for the repair of craniomaxillofacial bone defects comprising an apparatus as in claim 1 and a bone replacement material, packaged together.

35. A kit as in claim 34 wherein the bone replacement material comprises precursors capable of being combined to form a low temperature-hardening gradually resorbable hydroxyapatite forming cement.

36. A kit for the repair of craniomaxillofacial bone defects comprising an apparatus as in claim 32 and a bone replacement material packaged together.

37. A kit as in claim 36 wherein the bone replacement material comprises precursors capable of being combined to form a low temperature-hardening gradually resorbable hydroxyapatite forming cement.

* * * * *